US005560908A

United States Patent [19]
Satoh et al.

[11] Patent Number: 5,560,908
[45] Date of Patent: Oct. 1, 1996

[54] THERAPEUTIC AGENT FOR NIDDM

[75] Inventors: Jo Satoh; Takayoshi Toyota, both of Sendai, Japan

[73] Assignee: Kanegafuchi Kagaku Kogyo Kabushiki Kaisha, Osaka, Japan

[21] Appl. No.: 183,346

[22] Filed: Jan. 19, 1994

[30] Foreign Application Priority Data

Jan. 22, 1993 [JP] Japan .................. 5-008868
Jan. 22, 1993 [JP] Japan .................. 5-008869
Dec. 28, 1993 [JP] Japan .................. 5-337225

[51] Int. Cl.$^6$ ............................................ A61K 45/05
[52] U.S. Cl. ............................................ 424/85.1
[58] Field of Search ............................................ 424/85.1

[56] References Cited

U.S. PATENT DOCUMENTS

| | | | |
|---|---|---|---|
| 4,684,623 | 8/1987 | Larrick et al. | 514/12 |
| 4,920,196 | 4/1990 | Aggarwal | 530/351 |

FOREIGN PATENT DOCUMENTS

| | | |
|---|---|---|
| 0456842 | 11/1991 | European Pat. Off. . |
| 3236329 | 10/1991 | Japan . |
| 449244 | 2/1992 | Japan . |
| 4112835 | 4/1992 | Japan . |
| 9207578 | 5/1992 | WIPO . |
| 9210210 | 6/1992 | WIPO . |

OTHER PUBLICATIONS

Jacob et al., PNAS, vol. 87, pp. 968–972, Feb. 1990.
Del Ray et al., PNAS vol. 86, pp. 5943–5947, 1989.
Aggarwal et al., J. Biol. Chem., vol. 260(4), pp. 2345–2354, 1985.
Iguchi et al., Chem. Pharm. Bull., vol. 40(4), pp. 1004–1006, 1992.
Carswell et al., PNAS, vol. 72(9), pp. 3666–3670, 1975.
Anne Hamblin, "Lymphokines", IRL Press, pp. 48–51, 1988.
Bone, Roger C, Annals of Internal Medicine, vol 115(6), pp. 457–469, 1991.
Glauser, M. P. et al., The Lancet, vol. 338, pp. 732–736, 1991.
Kilbourn, Robert A. et al., Jour. of the National Cancer Institute, vol. 84(11), pp. 827–831, 1992.
Natanson, Charles et al., Annals of Internal Medicine, vol. 120(9), pp. 771–783, 1994.
The Economist, "Panic in the Petri Dish", pp. 61–62, Jul. 23, '94.
Cross, Alan S et al., Infection and Immunity, vol. 61, No. 7, pp. 2741–47, Jul. 1993.
Petros, Andy et al., The Lancet, vol. 338, pp. 1557–1558, 1991.
Old, Science, vol. 230, pp. 630–632, 1985.
Bendtzen et al., *Science*, "Cytotoxicity of Human pI 7 Interleukin–1 for Pancreatic Islets of Langerhans," vol. 232, 20 Jun. 1986, pp. 1545–1547.
Tracey, Kevin J. et al., Science, vol. 234, pp. 470–474, 1986.
Zeirath J. R. et al., Sports Med., vol. 14(3), pp. 171–189, 1992.
Shun–ichi Tanaka et al., Clin. Immunol. and Immunopathol., vol. 62(3), pp. 258–263, Mar. 1992.

*Primary Examiner*—Chhaya D. Sayala
*Attorney, Agent, or Firm*—Birch, Stewart Kolasch & Birch, LLP

[57] ABSTRACT

A therapeutic agent for and the treatment of NIDDM which comprises a cytotoxic cytokine or an inducer of a cytotoxic cytokine, as the effective ingredient.

9 Claims, 5 Drawing Sheets

THERAPEUTIC AGENT FOR NIDDM

BACKGROUND OF THE INVENTION

The present invention relates to a therapeutic agent for Non-Insulin-Dependent Diabetes Mellitus (NIDDM).

Diabetes is mainly classified to two types, i.e. Insulin-Dependent Diabetes Mellitus (IDDM) and NIDDM (ref. Kosaka J., "The classification of disease based on the concept of Diabetes Mellitus", Nippon Rinsho 1990 extra number, Diabetes Mellitus, Nippon Rinsho Press, Osaka 1990, p. 161–168). IDDM is a severe disease which attacks mainly the infant with symptoms of polyuria or polyposia suddenly. Since a patient with IDDM suffers from an absolute deficiency of insulin, he dies due to ketosis unless he is added an adequate quantity of insulin.

On the other hand, NIDDM is Diabetes showing relative slight symptoms, which attacks slowly the overweight adult. The number of patient with NIDDM is large and it is said that in Japan more than 90% of patients who suffer from Diabetes show NIDDM and the number of them is two million.

IDDM and NIDDM are different in their causes. It was shown by studies using IDDM model animals such as NOD mouse-or BB rat that β-cells in the pancreas which produce insulin are selectively killed by autoimmune in IDDM (ref. Satoh J., "Diabetes and immunity", Diabetes Frontier 1, 9–22 (1990)). Furthermore, it was reported that in these animals various immunotherapies related to processes of immune responses, such as an introduction of a normal gene of class II histocompatibility antigen, an enucleation of thymus, a transplant of normal bone marrow, an administration of various antibodies against T-cell or an administration of non-specific immunosuppressive agent, suppress a development of Diabetis, and furthermore, applications of their therapies to human IDDM have been progressing (ref. Satoh J. et al, "Current status of prevention and treatment of diabetic complications", Elsevier Science Publishers BV, Amsterdam, 1990, p. 658–661).

The present inventors have found that a nonspecific immune stimulation by an administration of immunopotentiator (ref. Toyota T. et al, Diabetes 35, 496–499 (1988) and Satoh J. et al, Diabetes 37, 1188–1194 (1988)) or by an administration of lymphotoxin (LT) (ref. Satoh J. et al., Japanese Unexamined Patent Publication No. 112835/1992 and Seino H. et al, Diabetes (in press)) or tumour necrosis factor (TNF) (ref. Satoh J. et al, J. Clin. Invest. 84, 1345–1348 (1989), Satoh J. et al, J. Immunol. 145, 1395–1399 (1990) and Seino H. et al, Clin. Exp. Immunol. 86, 413–418 (1991)) which are cytokines, suppressed the induction of cytotoxic lymphocytes which damage β-cells in the pancreas (ref. Shintani S. et al, J. Immunol. 144, 136–141 (1990)), so that the administration could protect the development of Diabetes in NOD mouse or BB rat.

On the other hand, NIDDM is characterized by a decrease in sensitivity to insulin, which is caused by a disorder of insulin production and secretion, existence of substances which suppress the action of insulin, a disorder of insulin receptors, a relative deficient of insulin by disorder of sites and signal transductions for insulin-action. Its complicated since it relates to both genetic factors and environmental factors. Obesity or aging is considered as an important factor which causes the decrease of sensitivity to insulin. As to a mechanism of the decrease of sensitivity to insulin, various disorders in some processes, from a process wherein insulin binds to the insulin receptors on the cell membranes to a process wherein the action of insulin is exhibited via a transmission of the information into cells, have been solving (ref. Kiyokawa Y. et al, Nippon Rinsho 1990 extra number, Diabetis Mellitus, Nippon Rinsho Press, Osaka 1990, p. 196–202).

Then, various agents as therapeutic agents for NIDDM, for example, (1) stimulants for synthesis of insulin and regulators for secretion of it as agents for disorder of the secretion and the production, (2) agents for absorption of sugar, stimulants for the utilization, agents for glucose transportor, or suppressors of gluconeogenesis in liver as agents for regulation of hyperglycemia, (3) stimulants for the action of insulin or antiglycation agents as a suppressor for disorder caused by hyperglycemia, and other anti-complication agents, have been developed, nevertheless, an effective therapy has not existed.

As the above mentioned, the mechanism of development of NIDDM is complicated, and an established theory of the mechanism thereof not has been obtained, a result, an effective protection against or therapy treatment for NIDDM has not been previously achieved.

Recently, it was found that hyperglycemia in an NIDDM model animal, KK-Ay mouse was normalized by bone marrow transplantation from a normal mouse (ref. Than S. et al, J. Exp. Med. 176, 1233–1238 (1992)) as well as allogeneic bone marrow transplantation to an IDDM model animal, NOD mouse could protect the development of Diabetes or inflammation of islets of Langerhans (ref. Nakamura M. et al, Diabetologia 3, 212–221 (1967) and Iwatsuka H. et al, Diabetologia 10, 611–616 (1974)).

An object of the present invention is to provide a therapeutic agent for NIDDM which is useful for immunological treatment in a short time or for a long time.

SUMMARY OF THE INVENTION

It has now been found that an administration of cytotoxic cytokines such as lymphotoxin (hereinafter referred to as LT) (ref. Ruddle N. H. and Waksman B. H., Science 15(7), 1060 (1967) or tumor necrosis factor (hereinafter referred to as TNF) (ref. Carswell E. A. et al, Proc. Nat. Acad. Sci. U.S.A. 72, 3666–3670 (1975)) which have extensive cytotoxic activity against tumor, or an administration of BCG which has inductive activity of the above cytokines, is significantly effective in protecting against and in the therapeutic treatment of NIDDM, which is never considered from the conventional function (cytotoxicity) which is recognized therefor.

The present invention provides a therapeutic agent for treating NIDDM comprising a cytotoxic cytokine as an effective ingredient.

Further the present invention provides a therapeutic agent for treating NIDDM comprising an inducer of a cytotoxic cytokine as an effective ingredient.

DETAILED DESCRIPTION

The cytotoxic cytokines in this specification mean not only the above LT and TNF which can easily be isolated but also various bioactive substances which have cytotoxic activities including apoptosis of the immunocompetent cells such as lymphocyte, monocyte, macrophage, NK cells or LAK cells or which are proteins or glycoproteins produced by the above cells and referred to as cytokine.

In addition, the above cytotoxic cytokines include natural types of cytokines which are obtained by causing animal cells to generate with a gene engineering technique, recombinant cytokines which are obtained from E. coli recombined with a gene which codes a part of a protein of a natural type of cytokine, polymer cytokines which are obtained by the aggregation or cross-linking of natural types of cytokine and recombinant cytokine, and active site of cytokine, and which are obtained as a polymer by the aggregation or cross-link of active sites of cytokine or active site. The cytotoxic cytokines also include both types of cytokine with and without sugar-moieties and recombinant modified cytokine. Furthermore, any body liquid introduced by the cytotoxic cytokines is also included.

The cytotoxic cytokines have quick effects in hyperglycemia compared with the effects by the inducers thereof and they have some advantages because they are non-persistent, such that they have little possibility of causing side effects such as hypoglycemia.

As such cytotoxic cytokines, there are, for example, LT, TNF and the like.

The use of LT (ref. Satoh J. et al, Japanese Unexamined Patent Publication No. 112835/1992 and Seino H. et al, Diabetes (in press)) or TNF (ref. Satoh J. et al, J. Clin. Invest. 84, 1345–1348 (1989), Satoh J. et al, J. Immunol. 145, 1395–1399 (1990) and Seino H. et al, Clin. Exp. Immunol. 86, 413–418 (1991)) is particularly preferred since they have effects on not only IDMM but also NIDDM.

The inducers of cytotoxic cytokines in this specification mean substances that can induce the above cytotoxic cytokines from immunocompetent cells such as lymphocyte, monocyte, macrophage, NK cells or LAK cells.

As such inducers of cytotoxic cytokines, there are, for example, 1) mycelium such as BCG (Bacille de Calmette et Guérin), 2) component of mycelium and inducers thereof such as vaccine of whooping cough, vaccine of diphtheria and lipoteichoic acid, 3) lectin which stimulates T-cell, such as Con A, 4) low molecular weight components which have immunopotential activities such as muramildipeptide (MDP) of which molecular weight is less than ten thousand and which can induce cytotoxic cytokines by activating immunocompetent cells and 5) some antigens, in case an organism is already sensitized by some antigens, particularly sensitized by the antigens which can introduce cell-mediated immunity. The effect of the administration of an inducer of a cytotoxic cytokine such as BCG in hyperglycemia persists for a long period as compared with the administration of cytotoxic cytokines.

The cytotoxic cytokines or inducers thereof used in the present invention can suppress a binding of sugar to proteins by regulating the hyperglycemia and can protect the various complications due to NIDDM, and can alleviate a reabsorption of sodium in vessel and can protect against hypertension due to hyperinsulinemia by regulating the hyperinsulinemia.

The cytotoxic cytokines for instance, LT or TNF, used in the present invention can be prepared by some processes, for example, 1) purification of body liquid 2) purification of supernatant obtained from a Chinese hamster oocyte culture medium (ref. Japanese Unexamined Patent Publication No. 11095/1987) 3) purification of supernatant of human B cell culture medium, which is transformed by EB virus (Aggarwal et al, J. Biol. Chem. 259, 686 (1984)) or 4) binding of protein produced by E. coli to sugar moieties.

On the other hand, the inducer of a cytotoxic, for instance, BCG used in the invention can be prepared by lyophilizing a suspension of mycelium culture medium obtained by culturing BCG in aseptic conditions.

The body liquid in this specification means blood, plasma, serum, ascites fluid, lymph, synovial fluid and components obtained from fractions thereof and humoral components derived from other organism.

The properties of LT and TNF as proteins is reported by Aggarwal (res. J. Biol. Chem. 260, 245 (1985) and J. Biol. Chem. 259, 686 (1984)) and the property of BCG as a inducer of cytotoxic cytokines is reported by Satoh J. et al (ref. J. Biol. Resp. Modif. 5, 117–123 (1986)).

The therapeutic agent for NIDDM in the present invention can be used in various preparation forms such as for injection and as in oral agent. These various preparations can be prepared in usual methods by using conventional additives which are generally used in the field of pharmaceutical preparation such as an excipient, binder, solvent, solubilizer, emulsifier or suspending agent according to the purpose of the treatment.

As such additives, there are, for example, lactose, sucrose, glucose, starch, crystalline cellulose, hydroxpropylmethylcellulose, carboxymethylcellulose, arabic gum, gelatin, magnesium alumino meta silicate, anhydrous calcium phosphate, citric acid, sodium citrate, hydroxypropylmethylcellulose, sorbitol, sorbitan esters of fatty acids, polyvinylpyrrolidone, vegetable oils such as peanut oil, olive oil and the like, benzyl alcohol, propylene glycol, water and the like.

The therapeutic agent for MDDM containing LT or TNF as a cytotoxic cytokines in the present invention can be administered by the usual administration routes and in particular intravenous injection or oral administration is preferred.

On the other hand, the therapeutic agent for NIDDM containing BCG as a inducer in the invention can also be administered by the usual administration routes and in particular intravenous injection or intraperitoneal injection is preferred.

LT, TNF or BCG is dissolved in liquid such as saline, ringer's solution and the like to admister. In case it is administered for the purpose of targetting for liver, it is dissolved in liquid such as saline, ringer's solution with a liposome, for example, a liposome having asialo GM on the surface.

The cytotoxic cytokines used in the present invention can be chosen from a range of $10^4$–$10^9$ units/day as an effective ingredient for human.

In case of LT or TNF it can be chosen from a range of $10^4$–$10^8$ units/day as an effective ingredient for human when it is administered as an intravenous injection. The unit of LT and TNF used in the present invention follows Yamazaki's method (ref. Yamazaki S., Onishi E. et al, Japanese Journal of Medical Science & Biology 39, 105 (1986)). Each $LD_{50}$ value of LT and TNF is 100,000 units/head in case that it is administered as an intravenous injection.

The inducers of the cytotoxic cytokines used in the present invention can be chosen from a range of 0.1 μg/day - 1 g/day as an effective ingredient for human. In case of BCG it can be chosen from 0.1 μg/day - 1 mg/day as an effective ingredient for human when it is administered as an intravenous injection. The unit of BCG (mg) follows the pharmacopoeia of Japan.

The present invention is more specifically described and explained by means of the following Preparation Examples and Examples. It is to be understood that the present invention is not limited to the Examples, and various changes and modifications may be made in the invention without departing from the spirit and scope thereof.

According to the following prescriptions the solutions for injection which contain the cytotoxic cytokines were prepared.

Preparation Example 1

| Glycosylated LT | 25,000 U |
|---|---|
| Saline (Japanese Pharmacopoeia) | 1 ml |
| Total | 1 ml |

Preparation Example 2

| TNF | 25,000 U |
|---|---|
| Saline (Japanese Pharmacopoeia) | 1 ml |
| Total | 1 ml |

Reference Preparation Example 1

| Interleukin-2 (IL-2) | 5,000 U | 50,000 U |
|---|---|---|
| Saline (Japanese Pharmacopoeia) | 1 ml | 1 ml |
| Total | 1 ml | 1 ml |

Reference Preparation Example 2

| mouse Interferon-γ (IFN-γ) | 5,000 U | 50,000 U |
|---|---|---|
| Saline (Japanese Pharmacopoeia) | 1 ml | 1 ml |
| Total | 1 ml | 1 ml |

Reference Preparation Example 3

| Insulin lente MC (40 units/ml) | 0.15 ml |
|---|---|
| Saline (Japanese Pharmacopoeia) | 2.85 ml |
| Total | 3.00 ml |

Note:
Glycosylated LT: commercially available from Kanegafuchi Kagaku Kogyo Kabushiki Kaisha
TNF: commercially available from Hayashibara Biochemical Laboratories, Inc.
IL-2 and mouse IFN-τ: commercially available from Shionogi & Go., Ltd.
Insulin lente MC: commercially available from Nobo. Co.

According to the following prescriptions the solutions for injection which contain the inducers of the cytotoxic cytokines were prepared.

Preparation Example 3

| BCG | 1 mg |
|---|---|
| Saline (Japanese Pharmacopoeia) | 1 ml |
| Total | 1 ml |

Reference Preparation Example 4

| Lentinan | 1 mg |
|---|---|
| Saline (Japanese Pharmacopoeia) | 1 ml |
| Total | 1 ml |

Note:
BCG: commercially available from Nippon BCG Co., Ltd.
Lentinan: commercially available from Ajinomoto Co., Ltd.

EXAMPLE 1

[Blood glucose value after GTT and cytokine administration]

Male KK-Ay/Takcl mice (commercially available from Nippon Clea, 8–20 weeks old, 25–30 g in body weight at the beginning of administration) were intraperitoneally injected with either 0.2 ml of saline solution or 0.2 ml of each cytokine solution for injection prepared according to the Preparation Example 1, 2 and Reference Preparation Example 1, 2. Then they were fasted and 5 hours later GTT was performed, i.e., they were intraperitoneally injected with 20% of glucose solution (2 g/kg body weight). Just before the administration of saline solution or cytokine solution, just before the administration of 20% of glucose solution and 1 hour after the administration of glucose solution, wounds were made in thieir tails by an injection needle to collect 20 μl of blood for determination of a blood glucose value. Each of the collected blood samples was diluted so that the blood glucose values may be calculated from measured values of the diluted blood with a calibration curve and each of the diluted blood samples was measured according to a glucose oxidase method by a device for measuring blood glucose (Lefrorax, made by Boehringer-Mannheim Co., Ltd. ). Sensitivity of the device is within a range from 10 to 500 mg/dl. The results are shown in Table 1. Each of data in Table 1 means an average and standard deviation for 5 mice in each treatment.

TABLE 1

| Treatment of Mice | Dose of Cytokines (LMU/head) | Blood Glucose (mg/dl) Time (h) after Glucose Administration | | |
|---|---|---|---|---|
| | | −5 | 0 | 1 |
| Saline | — | 259 ± 91 | 183 ± 6 | 461 ± 57 |
| LT | 5,000 | 266 ± 110 | 64 ± 10** | 215 ± 44** |
| Saline | — | | 190 ± 17 | 339 ± 79 |
| TNF | 5,000 | | 135 ± 30* | 192 ± 110* |
| Saline | — | | 195 ± 41 | 357 ± 99 |
| IL-2 | 1,000 | | 189 ± 20 | 368 ± 91 |
| | 10,000 | | 178 ± 16 | 364 ± 83 |
| Saline | — | | 196 ± 25 | 350 ± 54 |
| mouse IFN-γ | 1,000 | | 152 ± 7 | 315 ± 20 |
| | 10,000 | | 167 ± 10 | 324 ± 35 |

Note:
*$P < 0.05$
**$P < 0.01$

KK-Ay mice which have the insulin resistance, spontaneously develop NIDDM and they have been characterized by hyperinsulinemia and hyperglucosemia showing blood glucose values of generally two or three times as high as that of normal mice, from about 9 weeks old to about 16 weeks old. As shown in Table 1, not only the blood glucose values of the mice fasted after LT administration were decreased, but also an increase of the value in GTT was suppressed. It was also clearly shown that TNF had a LT like effect but blood glucose levels were not decreased by the treatment of IL-2 and mouse IFN-τ.

Furthermore, it was recognized that the improvement of glucose tolerance of LT and TNF was not characteristic to KK-Ay mice and was exhibited in other NIDDM model animals, for example, GK rat which was characterized by exhibiting a symptom of hyposecretion of insulin and depression of sensibility to insulin.

As above mentioned, it was found that the therapeutic agents of the present invention containing the cytotoxic cytokine, for example, LT or TNF as an effective ingredient were effective as the therapeutic agent for NIDDM caused by the various factors.

EXAMPLE 2

[Effect of the treatment with LT on GTT in KK-Ay mice and normal mice]

Male KK-Ay/Takcl mice (commercially available from Nippon Clea, 9 weeks old, 25–30 g in body weight at the beginning of administration) and male BALB/c mice (commercially available from SLC, 9 weeks old, 20–25 g in body weight at the beginning of administration) were intraperitoneally injected with either 0.2 ml of saline solution or 0.2 ml of LT solution prepared according to Preparation Example 1. Then they were fasted and 5 hours later GTT was performed, i.e., they were intraperitoneally injected with 20% of glucose solution (2 g/kg body weight). Just before the administration of saline solution or LT, just before the administration of 20% of glucose solution and 1, 19 hours after the administration of glucose solution, wounds were made in their tails by an injection needle to collect 20 μl of blood for determination of blood glucose values. Each of the collected blood samples was diluted so that the blood glucose values may be calculated from measured values of the diluted blood with a calibration curve and each of the diluted blood samples was measured according to a glucose oxidase method by a device for measuring blood glucose (Lefrorax, made by Boehringer-Mannheim Co., Ltd.). Sensitivity of the device is within a range from 10 to 500 mg/dl. The results are shown in Table 2 and FIG. 1. Each of data means an average and standard deviation of 3 mice in KK-Ay/Takcl mouse and of 6 mice in BALB/c mouse.

TABLE 2

| Mouse Strain | Treatment of Mice | Dose of LT (LMU/head) | Blood Glucose (mg/dl) Time (h) after Glucose Administration | | | |
|---|---|---|---|---|---|---|
| | | | −5 | 0 | 1 | 19 |
| KK-Ay | Saline | — | 357 ± 55 | 215 ± 29 | 370 ± 61 | 349 ± 30 |
| | LT | 50 | 340 ± 59 | 242 ± 60 | 413 ± 41 | 401 ± 73 |
| | | 500 | 323 ± 25 | 137 ± 24* | 212 ± 35* | 361 ± 98 |
| | | 5,000 | 278 ± 36 | 104 ± 35* | 181 ± 55* | 195 ± 130 |
| BALB/c | Saline | — | 132 ± 61 | 93 ± 31 | 141 ± 47 | NT** |
| | LT | 50 | 114 ± 24 | 91 ± 31 | 133 ± 14 | NT |
| | | 500 | 111 ± 27 | 97 ± 29 | 132 ± 89 | NT |
| | | 5,000 | 119 ± 42 | 80 ± 23 | 107 ± 33 | NT |

Note:
*P < 0.05
**NT: Not Tested

Figure 1:
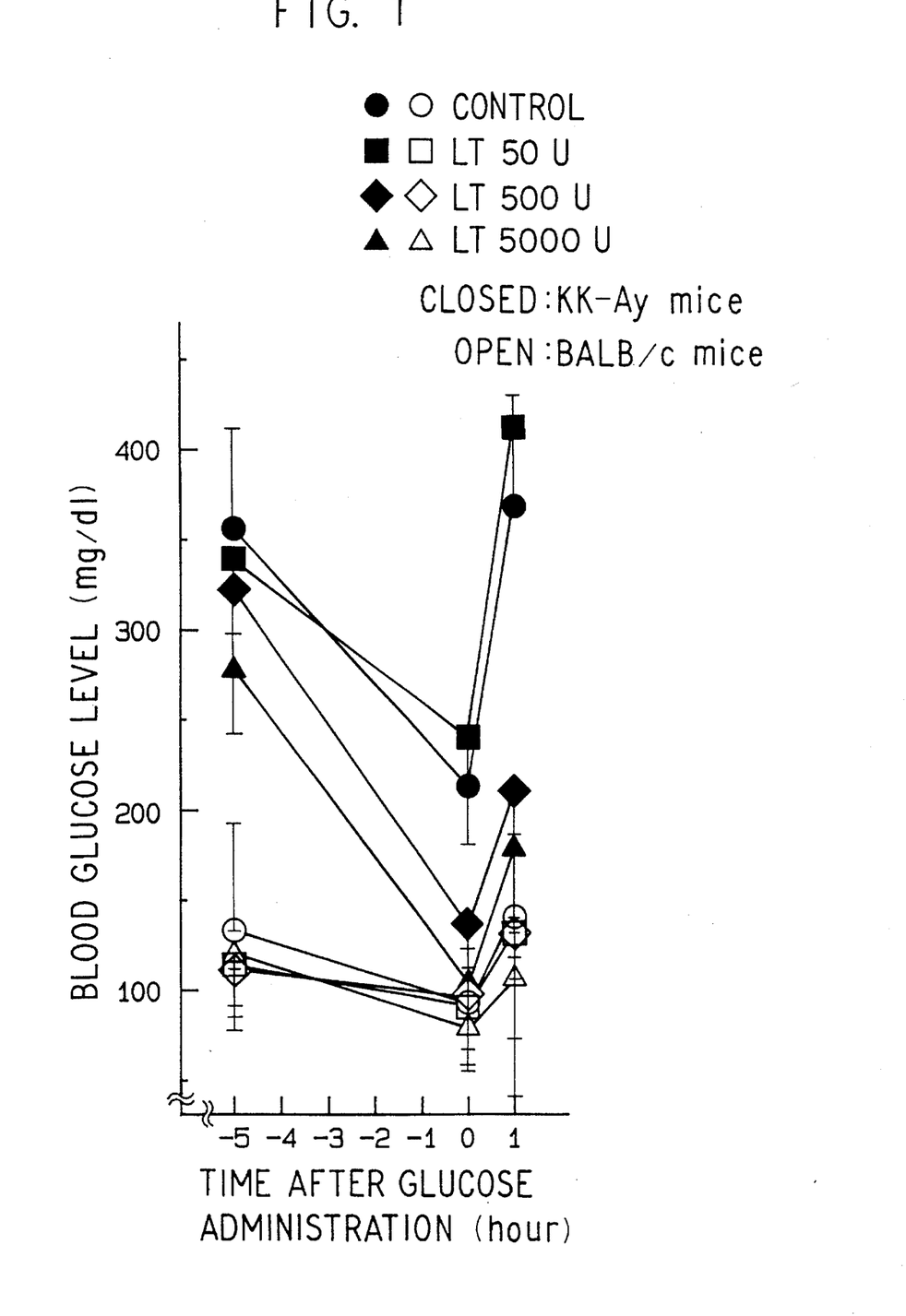
FIG. 1 is a graph showing effects of LT on blood glucose of the NIDDM model mice and the normal mice in Example 2.

As shown FIG. 1 and Table 2, LT exhibited a significant effect in the treatment with 500 to 5,000 units/head of LT though it is not clear in the treatment with 50 units/head of LT.

EXAMPLE 3

[Effect of the treatment with LT on Aging in KK-Ay mice]

Figure 2A:
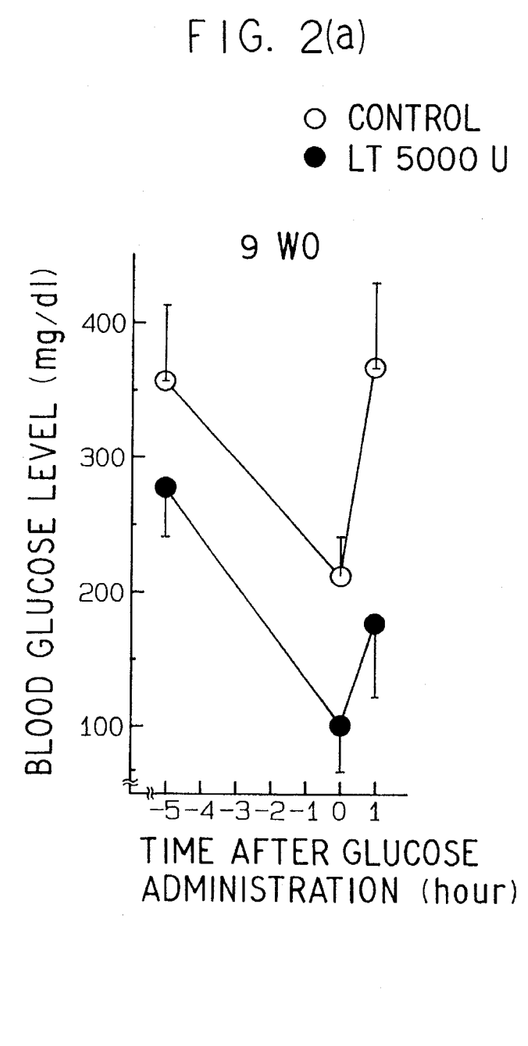
FIGS. 2(a) and 2(b) is a graph showing effects of LT on blood glucose of the NIDDM model mice (FIG. 2(a) 9 and FIG. 2(b) 16 weeks old) in Example 3.
Figure 2B:
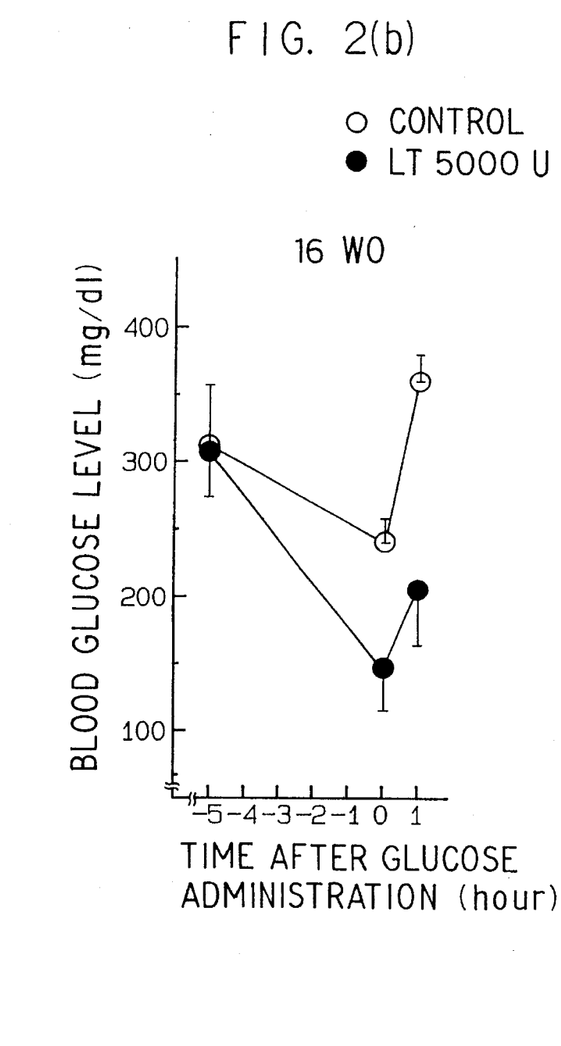

Male KK-Ay/Takcl mice (commercially available from Nippon Clea, 9 weeks old or 16 weeks old, 25–30 g in body weight at the beginning of administration) were intraperitoneally injected with either 0.2 ml of saline solution or 0.2 ml of LT solution prepared according to Preparation Example 1. Then they were fasted and 5 hours later GTT was performed, i.e., they were intraperitoneally injected with 20% of glucose solution (2 g/kg body weight). Just before the administration of saline solution or LT solution, just before the administration of 20% of glucose solution and 1 hour after the administration of glucose solution, wounds were made in their tails by an injection needle to collect 20 μl of blood for determination of blood glucose values. Each of the collected blood samples was diluted so that the blood glucose values may be calculated from measured values of the diluted blood with a calibration curve and each of the diluted blood samples was measured according to a glucose oxidase method by a device for measuring blood glucose (Lefrax, made by Boehringer-Mannheim Co., Ltd.). Sensitivity of the device is within a range from 10 to 500 mg/dl. The results are shown in Table 3 and FIG. 2. Each of data means an average and standard deviation of 3 mice in a group of 9 weeks old mice and 5 mice in a group of 16 weeks old mice.

TABLE 3

| Age (weeks) | Treatment of Mice | Dose of LT (LMU/head) | Blood Glucose (mg/dl) Time (h) after Glucose Administration | | |
|---|---|---|---|---|---|
| | | | −5 | 0 | 1 |
| 9 | Saline | — | 357 ± 55 | 215 ± 29 | 370 ± 61 |
| 9 | LT | 5,000 | 278 ± 36 | 104 ± 35* | 181 ± 55* |
| 16 | Saline | — | 312 ± 44 | 242 ± 17 | 361 ± 20 |
| 16 | LT | 5,000 | 308 ± 34 | 150 ± 31* | 208 ± 40* |

Note:
*p < 0.05

As shown in Table 3 and FIG. 2, LT exhibited an effect on a group of 16 weeks old mice as well as a group of 9 weeks old mice.

EXAMPLE 4

[Effect of the treatment with LT on fed KK-Ay mice or on fasted KK-Ay mice (Time course)]

The procedure of Example 2 was repeated except that other KK-Ay mice (the same condition as Example 2) were subcutaneously injected with 0.25 ml of insulin solution prepared according to Reference Preparation Example 3 and half of the number in the each group of mice administrated with either saline solution, LT solution or insulin solution were fed a pellet diet and water ad libitum and the rest were fasted for 24 hours, and that the measurements were performed just before the administration of saline solution, LT solution or insulin solution and 1,2,3,5,7,24 hours after the administration.

Figure 3A:
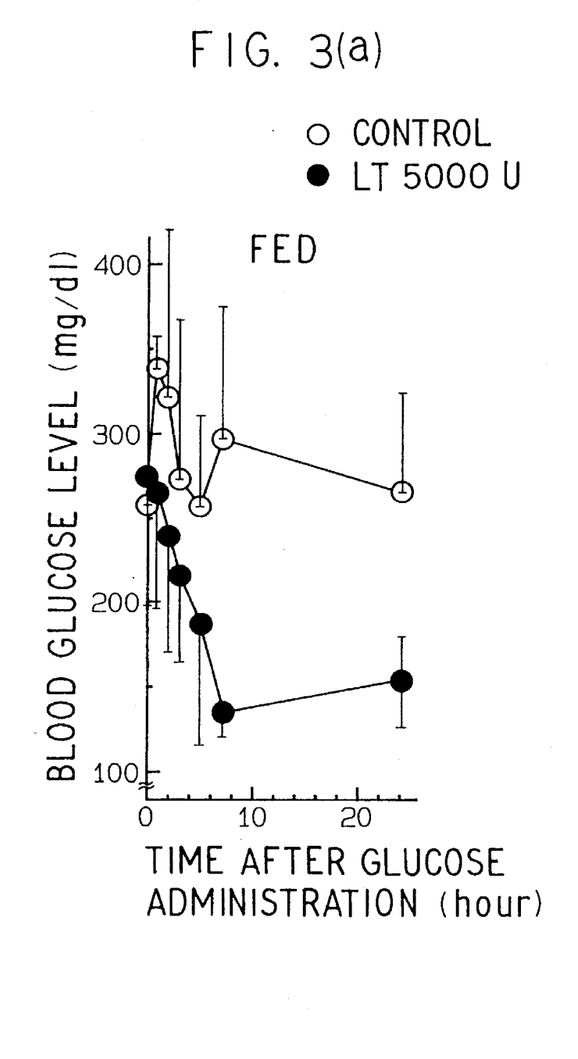
FIGS. 3(a) and 3(b) are graphs showing effects of LT on blood glucose of the NIDDM model mice (FIG. 3(a) fed ad libitum and FIG. 3(b) fasted after the administration of LT) in Example 4.
Figure 3B:
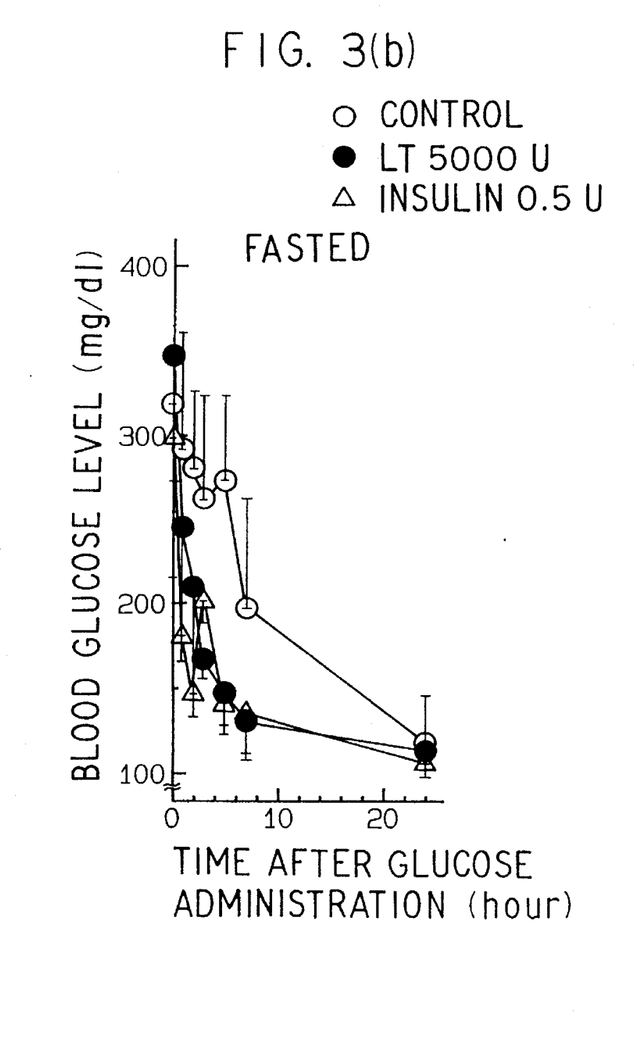

The results are shown in Table 4 (only the data of the mice fed ad libitum) and FIG. 3. In FIG. 3, each data shows an average and standard deviation of 3 mice.

TABLE 4

| Treatment of Mice | Dose of LT (LMU/head) | Blood Glucose (mg/dl) Time (h) after LT Administration | | | | | | |
|---|---|---|---|---|---|---|---|---|
| | | 0 | 1 | 2 | 3 | 5 | 7 | 24 |
| Saline | — | 255 ±92 | 334 ±19 | 318 ±97 | 270 ±93 | 254 ±54 | 294 ±76 | 264 ±58 |
| LT | 5,000 | 271 ±75 | 262 ±69 | 237 ±69 | 213 ±51 | 185 ±70 | 134* ±14 | 153* ±26 |

Note:
*P < 0.05

As shown in FIG. 3, LT decreased rapidly the blood glucose level to the normal level of BALB/C mouse in Table 2 within 7 hours in both the group of the mice fed ad libitum and the group of the fasted mice. Furthermore, the effect of LT on the group of the mice fed ad libitum maintained for at least 24 hours after the administration and on the other hand the effect of LT on the group of the fasted mice was correspondent to 0.5 units of insulin (the half lethal dose of insulin) within 7 hours.

Since the blood glucose value of the group of the control mice injected with saline solution decreased to the normal level 24 hours after the administration, the effect of LT could not be estimated.

The effect of LT on blood lipids was examined with the group of the fasted mice. As a result, no changes of TG- and FFA-level were observed except that a slight increase of TG at 24 hours after the treatment of LT was found. The effect of insulin on TG was not observed (Data not shown).

EXAMPLE 5

[Effect of LT on releasing endogenous insulin]

Figure 4A:
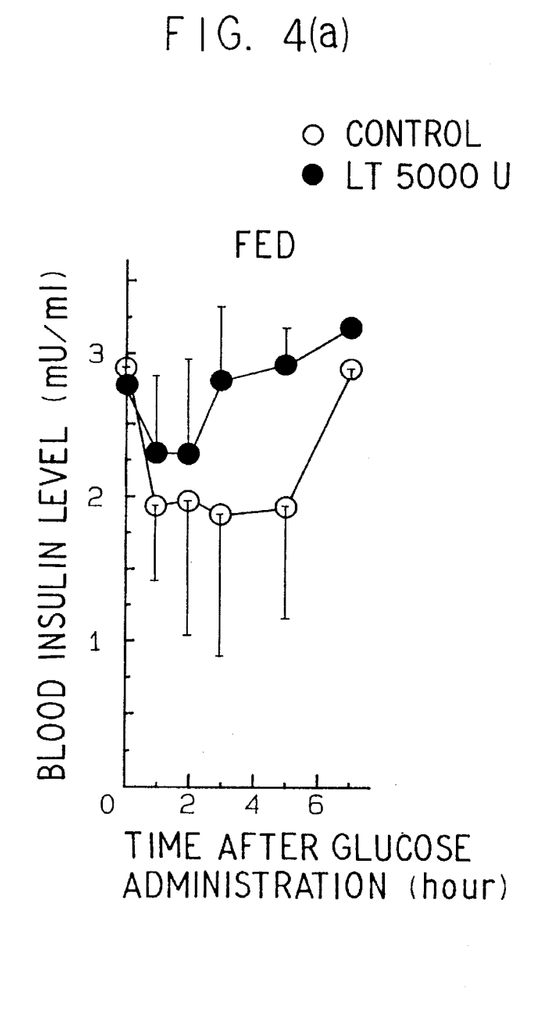
FIGS. 4(a) and 4(b) are graphs showing effects of LT on blood insulin of the NIDDM model mice (FIG. 4(a) fed ad libitum and FIG. 4(b) fasted) in Example 5.
Figure 4B:
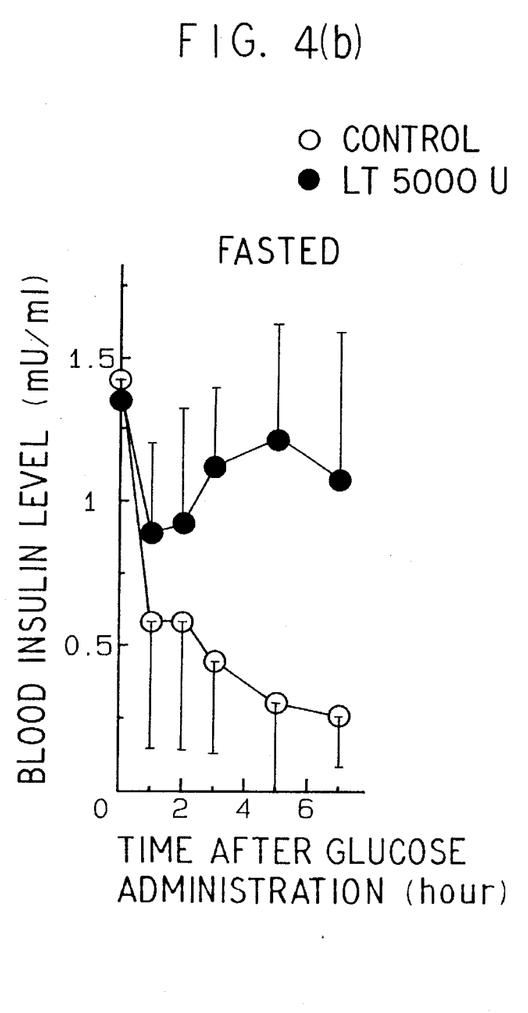

Male KK-Ay/Takcl mice (commercially available from Nippon Clea, 9 weeks old, 25–30 g in body weight at the beginning of administration) were intraperitoneally injected with either 0.2 ml of saline solution or 0.2 ml of LT solution prepared according to the Preparation Example 1. Then, half of the each group of the mice were fed a pellet diet and water ad libitum and the rest were fasted for 24 hours, and determinations of blood insulin were performed. Just before the administration of saline solution or LT solution, and 1,2,3,5 and 7 hours after the administration, wounds were made in their tails by an injection needle to collect 20 μl of blood. Each of the collected blood samples was diluted so that the blood insulin values may be calculated from measured values of the diluted blood with a calibration curve and each of the diluted blood samples was measured according to Enzyme-Linked Immunosorbent Assay (ELISA) by using a immunoball IRI neo (commercially available from Toyobo and Ono Yakuhin Kogyo Kabushiki Kaisha). Sensitivity of the assay is within a range from 10 to 320 μU/ml. The results are shown in Tables 5, 6 and FIG. 4. In Table 5 the data of the mice group fed ad libitum was and in Table 6 the data of the fasted mice group was plotted against time respectively. Each data shows an average and standard deviation of 5 mice.

TABLE 5

| Treatment of Mice | Dose of LT (U/head) | Blood Insulin (μ U/ml) Time (h) after LT Administration | | | | | |
|---|---|---|---|---|---|---|---|
| | | 0 | 1 | 2 | 3 | 5 | 7 |
| Saline | — | 2,896 ±417 | 1,944 ±517 | 1,976 ±928 | 1,884 ±964 | 1,944 ±762 | 2,916 ±74 |
| LT | 5,000 | 2,768 ±524 | 2,300 ±536 | 2,300 ±660 | 2,806 ±517 | 2,926* ±262 | 3,186* ±31 |

Note:
*p < 0.05

Table 6

| Treatment of Mice | Dose of LT (U/head) | Blood Insulin (μ U/ml) Time (h) after LT Administration | | | | | |
|---|---|---|---|---|---|---|---|
| | | 1 | 2 | 3 | 4 | 5 | 7 |
| Saline | — | 1,417 ±311 | 583 ±432 | 585 ±435 | 453 ±314 | 313 ±315 | 275 ±174 |
| LT | 5,000 | 1,340 ±363 | 888 ±309 | 928 ±395 | 1,120* ±275 | 1,224* ±397 | 1,080* ±520 |

Note:
*P < 0.05

The rapid decrease of blood insulin level after the administration of saline solution and the subsequential decline were observed in the control group of the fasted mice. On the other hand, the insulin level of the group of the fasted mice group was maintained the same level as one before it was fasted though there observed a little lagtime.

In case of feeding ad libitum, the blood insulin of the control group of mice was not decreased so much due to the stimulation of insulin compared to the case of the group of the fasted mice and the blood insulin of the group of the mice treated with LT exhibited the higher value than that of the control at least 3 hours after the administration of LT. Thus, in case of the administration of saline solution, the blood insulin values are different from in the fasted condition and in the fed condition, but in case of the administration of LT, the same effect was shown in spite of the condition after the administration of LT.

EXAMPLE 6

[Effect of treatment with inducers of cytotoxic cytokines on GTT in KK-Ay mice]

Male KK-Ay/Takcl mice (commercially available from Nippon Clea, 8–20 weeks old, 25–30 g in body weight at the beginning of administration) were intraperitoneally injected with 0.2 ml of cytokine inducer solutions prepared according to Preparation Example 3 or Reference Preparation Example 4. BCG was injected once and Lentinan (IL-2 inducer) was injected one time per 2 days (total 3 times). Then they were fasted and 15 hours later 20% of glucose solution (2 g/kg body weight) was intrapritoneally injected. Just before the administration of 20% of glucose solution, and 1 hour after the administration, wounds were made in their tails by an injection needle to determine blood glucose values. The determination of the values was performed according to Example 1.

The results are shown in Table 7. The data in Table 7 mean an average and standard deviation of 5 or 6 mice.

TABLE 7

| Treatment of Mice | Dose (mg/head) | Blood Glucose (mg/dl) Time (h) after Glucose Administration | |
|---|---|---|---|
| | | 0 | 1 |
| Saline | — | 73 ± 12 | 452 ± 76 |
| BCG | 0.2 | 51 ± 10** | 170 ± 31** |
| Lentinan | 0.2 | 84 ± 12 | 431 ± 76 |

Note:
**P < 0.01

As shown in Table 7, blood glucose levels were decreased and an increase of blood glucose levels in GTT was inhibited by the treatment with BCG but not with Lentinan which is known as a inducer of IL-2.

EXAMPLE 7

[Effect of treatment with BCG on GTT in KK-Ay mice for long period]

Male KK-Ay/Takcl mice (commercially available from Nippon Clea, 8–20 weeks old, 25–30 g in body weight at the beginning of administration) were intraperitoneally injected with either 0.2 ml of saline solution or 0.2 ml of BCG solution prepared according to Preparation Example 3. All these mice were divided into four groups. 1 day, 1 weeks, 2 weeks, 4 weeks later, they were fasted for 12 hours, and then injected intraperitoneally with 20% of glucose solution (2 g/kg body weight).

On the other hand, other male KK-Ay/Takcl mice (the same conditions as the above) were fasted for 12 hours 1 day before the administration of 0.2 ml of BCG solution prepared according to Preparation Example 3. Then, the mice were intraperitoneally injected with 20% of glucose solution (2 g/kg body weight). Just before the administration of saline solution or BCG solution, just before the administration of 20% of glucose solution and 1 hour after the administration of glucose solution, the blood glucose values were determined in the same manner as Example 1.

Figure 5:
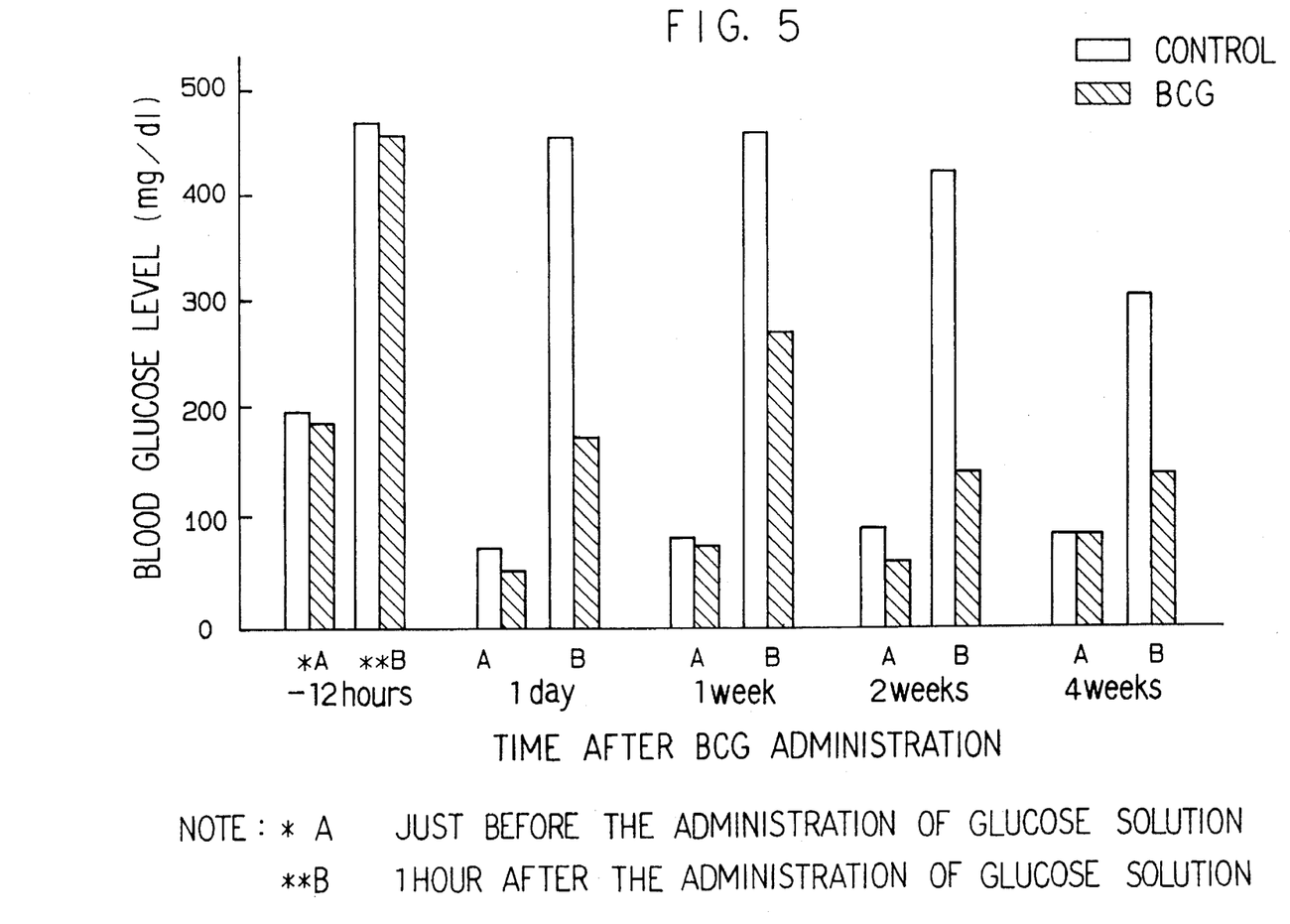
FIG. 5 is a graph showing effects of BCG on blood glucose of the NIDDM model mice in Example 7.

The results are shown in FIG. 5 in which each of data means an average of 5 mice in each treatment.

As shown in FIG. 5, effect of the treatment with BCG was maintained at least for 4 weeks.

The improvement of gluclose tolerance was not peculiar to KK-Ay mice and was observed in the other NIDDM model animals such as GK rat.

As the above mentioned, the therapeutic agent of the present invention which contains inducer of cytotoxic cytokine represented by BCG as an effective ingredient, exhibits effect as a therapeutic agent for NIDDM for a long time.

What we claim is:

1. A method of treating Non-Insulin-Dependent Diabetes Mellitus (NIDDM) in a patient, the method comprising administering to the patient a pharmaceutical composition comprising:

an effective amount of a lymphotoxin; and an additive therefor.

2. The method of claim 1, wherein the patient is a human and the lymphotoxin is administered to the patient in an amount of $10^4$–$10^9$ units/day.

3. The method of claim 1, wherein the patient is a human and the lymphotoxin is administered by intravenous injection to the patient in an amount of $10^4$–$10^8$ units/day.

4. A method of treating Non-Insulin-Dependent Diabetes Mellitus (NIDDM) in a patient, the method comprising administering to the patient a pharmaceutical composition comprising:

an effective amount of a glycosylated lymphotoxin; and an additive therefor.

5. The method of claim 4, wherein the patient is a human and the glycosylated lymphotoxin is administered to the patient in an amount of $10^4$–$10^9$ units/day.

6. The method of claim 4, wherein the patient is a human and the glycosylated lymphotoxin is administered by intravenous injection to the patient in an amount of $10^4$–$10^8$ units/day.

7. A method of treating Non-Insulin-Dependent Diabetes Mellitus (NIDDM) in a patient, the method comprising administering to the patient a pharmaceutical composition comprising:

an effective amount of tumor necrosis factor; and an additive therefor.

8. The method of claim 7, wherein the patient is a human and the tumor necrosis factor is administered to the patient in an amount of $10^4$–$10^9$ units/day.

9. The method of claim 7, wherein the patient is a human and the tumor necrosis factor is administered by intravenous injection to the patient in an amount of $10^4$–$10^8$ units/day.

* * * * *